US006974588B1

(12) United States Patent
Miranda et al.

(10) Patent No.: US 6,974,588 B1
(45) Date of Patent: Dec. 13, 2005

(54) TRANSDERMAL PATCH FOR DELIVERING VOLATILE LIQUID DRUGS

(75) Inventors: Jesus Miranda, Miami, FL (US); Charles J. Betlach, II, Pembroke Pines, FL (US)

(73) Assignee: Elan Pharma International Limited, Clare (IE)

( * ) Notice: Subject to any disclaimer, the term of this patent is extended or adjusted under 35 U.S.C. 154(b) by 0 days.

(21) Appl. No.: 09/456,278

(22) Filed: Dec. 7, 1999

(51) Int. Cl.[7] .................. A61F 13/02; A61F 13/00; A61L 15/16
(52) U.S. Cl. ..................... 424/448; 424/449
(58) Field of Search ............... 424/448, 449, 424/443; 514/343

(56) References Cited

U.S. PATENT DOCUMENTS

| 3,731,683 | A |   | 5/1973  | Zaffaroni ............... 128/268 |
| 3,797,494 | A |   | 3/1974  | Zaffaroni ............... 128/268 |
| 4,336,243 | A |   | 6/1982  | Sanvordeker et al. ...... 424/28 |
| 4,717,568 | A |   | 1/1988  | Eckenhoff et al. ........ 424/469 |
| 4,877,618 | A |   | 10/1989 | Reed, Jr. ............... 424/448 |
| 4,915,950 | A |   | 4/1990  | Miranda et al. .......... 424/448 |
| 5,004,610 | A | * | 4/1991  | Osborne et al. .......... 424/448 |
| 5,141,750 | A | * | 8/1992  | Lee et al. |
| 5,164,190 | A |   | 11/1992 | Patel et al. |
| 5,176,915 | A |   | 1/1993  | Hoffmann ............... 424/445 |
| 5,230,898 | A |   | 7/1993  | Horstmann et al. ........ 424/449 |
| 5,298,257 | A | * | 3/1994  | Bannon et al. ........... 424/449 |
| 5,316,759 | A | * | 5/1994  | Rose et al. |
| 5,350,581 | A |   | 9/1994  | Kochinke .............. 424/443 |
| 5,364,630 | A |   | 11/1994 | Osborne et al. .......... 424/449 |
| 5,411,739 | A |   | 5/1995  | Jaeger et al. ............ 424/448 |
| 5,574,052 | A |   | 11/1996 | Rose et al. ............. 514/343 |
| 5,603,947 | A | * | 2/1997  | Wong et al. ............. 424/447 |
| 5,656,286 | A | * | 8/1997  | Miranda et al. |
| 5,691,365 | A |   | 11/1997 | Crooks et al. ........... 514/343 |
| 5,721,257 | A | * | 2/1998  | Baker et al. |
| 5,726,190 | A |   | 3/1998  | Rose et al. ............. 514/343 |
| 5,762,952 | A |   | 6/1998  | Barnhart et al. ......... 424/448 |
| 5,914,282 | A | * | 6/1999  | Dunshee et al. .......... 442/76 |
| 6,090,404 | A | * | 7/2000  | Meconi et al. |
| 6,165,497 | A | * | 12/2000 | Osborne et al. .......... 424/447 |
| 6,264,977 | B1 | * | 7/2001 | Hoffmann |
| 6,316,022 | B1 |   | 11/2001 | Mantelle et al. ......... 424/448 |

FOREIGN PATENT DOCUMENTS

| EP | 321 870      | 12/1988 |
| EP | 0524776 A1   | 1/1993  |
| WO | WO 93/00058 A1 | 1/1993 |
| WO | WO 96/40085 A2 | 12/1996 |

OTHER PUBLICATIONS

Nangia et al., "High Dissociation Constants of Basic Permeants Are Associated In Vivo Skin Irritation In Man," Contact Dermatitis, 34;237-242 (1996).
Rose et al., "Nicotine/Mecamylamine Combination Treatment For Smoking Cessation," Drug Dev. Res., 38;243-256 (1996).
Rose et al., "Mecamylamine Combined With Nicotine Skin Patch Facilities Smoking Cessation Beyond Nicotine Patch Treatment Alone," Clin. Pharm. And Ther., 56(1); 86-99 (1994).

* cited by examiner

Primary Examiner—Gollamudi S. Kishore
Assistant Examiner—Isis Ghali
(74) Attorney, Agent, or Firm—Synnestvedt & Lechner LLP

(57) ABSTRACT

A transdermal patch for administering a volatile liquid drug, such as nicotine, transdermally to a patient comprising a four-layer laminated composite of: a top drug impermeable backing layer; a pressure sensitive silicone adhesive layer containing the drug; a pressure sensitive acrylic adhesive layer also containing the drug; and a removable siliconized release liner layer. Also disclosed is a method for treating a person for nicotine dependence and particularly for treating a woman for nicotine dependence.

3 Claims, 8 Drawing Sheets

Mean Nicotine Plasma Concentration by Treatment and Study Week

TRANSDERMAL PATCH FOR DELIVERING VOLATILE LIQUID DRUGS

TECHNICAL FIELD

This invention is in the field of transdermal drug delivery devices. More particularly, it relates to a method for making transdermal patches that deliver volatile liquid drugs, such as nicotine, mecamylamine and selegiline, and to the resulting patches. The invention also relates to a method for treating a person for nicotine dependence comprising transdermally administering an effective amount of mecamylamine to the person without transdermal coadministration of nicotine. The invention further relates to a method for treating women for nicotine dependence comprising transdermally co-administering effective doses of mecamylamine and nicotine.

BACKGROUND ART

There are two basic types of transdermal patches that are used to deliver liquid drugs. One is a liquid reservoir patch in which the liquid drug, either neat or dissolved in a carrier, is confined in a pouch or sac within the device. An example of such a device for delivering nicotine is shown in FIG. 1 of U.S. Pat. No. 5,364,630. The other is a matrix patch in which the liquid drug is dissolved in one or more polymeric layers of a laminated composite. Examples of matrix patches that deliver nicotine are described in U.S. Pat. No. 5,603,947. The present invention relates to a matrix patch.

In the manufacture of matrix patches for administering volatile liquid drugs such as nicotine it is common to attempt to avoid steps involving heat treatment, e.g., drying, so as to avoid excessive loss or degradation of the drug. For instance U.S. Pat. Nos. 4,915,950 and 5,603,947 describe a printing procedure whereby neat nicotine is applied to a nonwoven fabric laminated to a polyisobutylene adhesive layer. Alternatively "hot" melt adhesives that melt at relatively low temperatures have been used as a matrix material for these drugs. See U.S. Pat. No. 5,411,739.

PCT Pub. No. WO 96/40085 describes transdermal matrix patches for administering drugs such as selegiline, nitroglycerin and nicotine, that are liquid at normal room temperature. The publication suggests making a monolithic matrix of the drug in an adhesive by mixing one or more polymeric adhesives, preferably polyacrylate and polysiloxane, and the drug in a volatile solvent, casting the mixture, and evaporating the solvent. The publication lists as examples of volatile solvents isopropanol, ethanol, xylene, toluene, hexane, cyclohexane, heptane, ethyl acetate and butyl acetate.

When silicone adhesives have been used as the matrix material in nicotine patches the matrix layer has been cast from a heptane solution. See, for instance, Example 1 of U.S. Pat. No. 5,603,947. Other co-solvents, including hexane, have been suggested for use with silicone adhesives used in transdermal devices. See p. 3, line 51, et seq. of EPO 524776 A1.

Mecamylamine is an antagonist to nicotine. U.S. Pat. Nos. 5,316,759, 5,726,190, and 5,574,052 teach the coadministration of mecamylamine and nicotine to treat nicotine dependency. These patents do not teach or suggest the transdermal administration of mecamylamine itself to treat nicotine dependency. Furthermore, the prior art does not teach that coadministration of mecamylamine and nicotine is especially effective as a smoking cessation aid specifically suited for women.

DISCLOSURE OF THE INVENTION

One aspect of this invention is a transdermal patch for administering a volatile liquid drug transdermally to a patient comprising:
  a) a top backing layer that is impermeable to the drug;
  b) silicone adhesive layer containing the drug and underlying the backing layer;
  c) an acrylic adhesive layer also containing the drug that underlies and is in diffusional contact with the silicone adhesive layer; and
  d) a removable release liner layer underlying the acrylic adhesive layer, wherein the combined amount of drug in the silicone adhesive layer and the acrylic adhesive layer is sufficient to provide a therapeutically effective amount of drug to the patient.

Another aspect of the invention is a method of making a transdermal patch for administering a volatile liquid drug transdermally to a patient comprising:
  a) coating a solution of the drug and a silicone adhesive in hexane onto a backing layer;
  b) evaporating the hexane from the coating to form a silicone adhesive layer containing the drug; and
  c) laminating a polyacrylate adhesive layer affixed to a release liner layer onto the silicone adhesive layer such that the silicone adhesive layer and the acrylic adhesive layer are in diffusional contact with each other.

Another aspect of the invention is a method for treating a person for nicotine dependence comprising transdermally administering a therapeutically effective amount of mecamylamine without transdermal coadministration (or other coadministration except by smoking) of nicotine to the person.

A further aspect of the invention is a method for treating a woman for nicotine dependence comprising transdermally coadministering a therapeutically effective amount of nicotine and a therapeutically effective amount of mecamylamine.

MODES FOR CARRYING OUT THE INVENTION

As used herein the term "volatile liquid drug" intends a drug that (i) is capable of permeating through unbroken human skin at therapeutically effective rates from a patch of practical size, the permeation either being unenhanced or enhanced through coadministration of one or more skin permeation enhancing agents, (ii) is a liquid at 25° C. atmospheric pressure, and (iii) has a boiling point less than about 300° C. at atmospheric pressure. Examples of such drugs are nicotine, mecamylamine, selegiline, and nitroglycerine.

As used herein the term "diffusional contact" intends a relationship, either through direct contact or through indirect contact via an intermediary material, between two surfaces or layers such that drug is able to pass by diffusion from one surface or layer to the other surface or layer.

As used herein the term "treating a person for nicotine dependence" intends causing the person to reduce or eliminate his or her intake of nicotine from smoking and/or chewing tobacco on a temporary or permanent basis.

Figure 1:
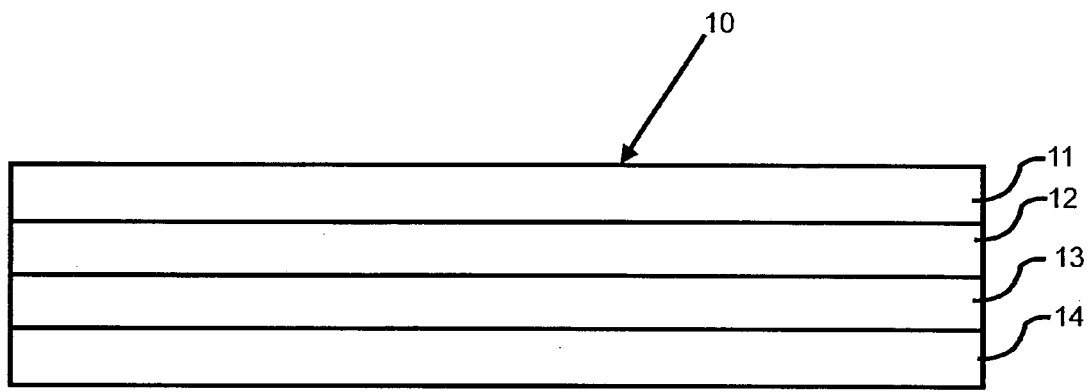
FIG. 1 is a elevational cross-sectional view of an embodiment of the invention patch.

The embodiment of the invention shown in FIG. 1 is a four-layer laminated composite matrix type transdermal patch, generally designated 10. The four layers are: (1) a top drug-impermeable backing layer 11; (2) an intermediate drug-containing silicone adhesive layer 12; (3) a basal drug-containing polyacrylic adhesive layer 13; and (4) a removable release liner layer 14.

Materials for making backing layer 11 are well known in the art. They include various polymers such as polyethylene terephthalate, polyethylene, polypropylene and polyvinyl chloride, metal foils such as aluminum foil, and polymer-metal composites.

Adhesive layer 12 is made from a pressure sensitive silicone adhesive. An amine compatible silicone adhesive is preferred for use with drugs, such as nicotine, which contain amine groups. These adhesives are described in detail in the Handbook of Pressure Sensitive Adhesive Technology, 2nd Edition, pp. 508–517 (D. Satas, ed.), Van Nostrand Reinhold, New York (1989). See also Pfister, W. R., et al. "Silicon Adhesives for Transdermal Drug Delivery" Chemistry in Britain (January 1991). pp. 43–46 and EP Pub. No. 0524776 A1. Suitable commercially available silicone pressure sensitive adhesives are available from Dow Corning under the trademark BIO-PSA. The silicone pressure sensitive adhesives are supplied commercially as solutions in a solvent. Per the present invention the solvent should be hexane. The thickness of layer 12 will usually be in the range of about 25 to 100 microns, more usually 50 to 75 microns. Expressed alternatively, the layer 12 will be present at about 4 to 18 mg/cm$^2$, more usually 8 to 14 mg/cm$^2$. Adhesive layer 12 initially (before it is laminated to adhesive layer 13) contains the entire drug loading. In this regard, the drug(s) will usually be added to the silicone adhesive in amounts ranging between about 5% to 50% by weight, more usually 10% to 30% by weight, based on the total dry weight of drug and adhesive.

Adhesive layer 13 is made from one or more solution acrylic pressure sensitive adhesives. These adhesives are described in detail in the Handbook of Pressure Sensitive Adhesive Technology, 2nd Edition, pp. 396–456 (D. Satas, ed.) Van Nostrand Reinhold, New York (1989). They are usually copolymers composed of: 50% to 90% of a main acrylate or methacrylate monomer, usually 2-ethylhexyl acrylate, butylacrylate, or iso-octyl acrylate; 10% to 40% of a modifying monomer such as vinyl acetate; and 2% to 20% of a functional group-containing monomer such as acrylic acid. Examples of suitable commercially available solution acrylic pressure sensitive adhesives are: National Starch DuroTak® adhesives 87-2194 and 87-2070. The thickness of the acrylic adhesive layer 13 will usually be about the same as that of layer 12. After lamination to the silicone adhesive layer 12 and equilibration of the drug between layers 12 and 13, layer 13 will also contain drug. In this regard the drug will usually constitute about 2.5% to 30% by weight, preferably 5% to 15% by weight, of layer 13 after equilibration occurs.

The release liner layer 14 is removed before device 10 is placed on the skin. After layer 14 is removed the lower surface of layer 13 is exposed and defines the basal surface of the device which is intended to be placed directly in contact with the skin. Release liner layers are well known in the transdermal patch art. They are made of materials that permit the layer to be easily stripped or peeled away from the adjacent pressure sensitive adhesive layer. Release liner layers are typically made from drug impermeable polymers such as polyesters which are coated with materials such as silicone or fluorinated hydrocarbons that reduce the adhesiveness between it and the adjacent pressure sensitive adhesive layer. In this regard since the acrylic pressure sensitive adhesive layer rather than the silicone pressure sensitive adhesive layer defines the basal surface of the device it is possible to use a siliconized release liner. Such liners are generally not compatible with silicone adhesives. Siliconized liners are more economical than fluorocarbon coated liners. Further, use of the acrylic pressure sensitive adhesive as the basal layer provides a more controlled and predetermined delivery of the drug than could be achieved using a silicone adhesive basal layer. The particular drug release profile from the patch can be varied by altering the thickness and/or composition of the acrylic pressure sensitive adhesive layer and/or the drug loading, and/or by employing a permeation enhancer.

The drug is released from the surface of the acrylic pressure sensitive adhesive to the skin at a therapeutically effective rate. That rate will depend upon the particular drug. In the case of nicotine, the rate will usually be in the range of 0.2 to 1.5 mg/hr, preferably 0.3 to 0.9 mg/hr. In the case of co-administration of nicotine and the mecamylamine, the nicotine rate will usually be in the range of 0.2 to 1.5 mg/hr, preferably 0.3 to 0.9 mg/hr, and the mecamylamine rate will usually be in the range of 0.02 to 1 mg/hr, preferably 0.1 to 0.6 mg/hr. In the case of mecamylamine alone, the rate will usually be in the range of 0.02 to 1 mg/hr, preferably 0.1 to 0.6 mg/hr. In the case of selegiline, the rate will usually be in the range of 0.2 to 3 mg/day. The flux (rate per unit area) of drug from the basal surface of the acrylic pressure sensitive adhesive and the area of that surface are matched to provide the desired rate of drug administration. As indicated, the flux may be varied by altering the drug loading, composition and/or thickness of the acrylic pressure sensitive adhesive layer, and/or by the use of permeation enhancers. The surface area of the layer in diffusional contact with the skin will usually be in the range of 5 to 100 cm$^2$, more usually in the range of about 10 to 50 cm$^2$. Each patch may be applied to the skin for periods of from several hours up to about a week, and more preferably for about 1 to 3 days.

The patches of the invention are made in the following manner. The drug(s) is dissolved in the desired proportion(s) in a hexane solution of the pressure sensitive silicone adhesive. The drug(s) will normally constitute about 2.5% to 25% by weight of the solution. This solution is then cast onto the backing layer and allowed to dry. By casting the drug and silicone adhesive from a hexane solution, very low casting and drying temperatures (30° C. to 40° C.) may be used, thus reducing degradation or loss of the liquid drug(s) during the casting and drying process. Even though low processing temperatures in the 30° C. to 40° C. range are used, low residual hexane levels (e.g., <0.1% by wt.) are found in the layer after about 1 to 5 min. of drying. Other solvents, such as heptane and toluene, are not suitable since they require higher processing temperatures and thus result in more drug degradation and/or evaporation during coating and drying. Other pressure sensitive adhesives such as acrylics or polyisobutylenes are similarly not suitable for formulating liquid drugs since they require higher processing temperatures to remove their solvents (e.g., ethyl acetate, heptane, etc.). The silicone adhesive also has excellent adhesion to the backing. A solution of the acrylic pressure sensitive adhesive is cast onto a siliconized release liner layer and permitted to dry. The acrylic pressure sensitive adhesive/release liner subassembly is then laminated to the drug-containing silicone pressure sensitive adhesive/backing subassembly to form the final laminated composite. After lamination the drug(s) equilibrates in the adjacent adhesive layers. Patches are cut/punched from the composite and placed in appropriate packaging.

Alternatively, the drug and silicone adhesive solution can be cast onto a disposable liner and dried as described. The sub-assembly can be laminated to the acrylic pressure sensitive adhesive/release liner subassembly. The disposable liner is then removed to expose the top surface of the silicone adhesive layer. A backing is then laminated to the top surface of the silicone adhesive layer to form the final laminated composite. In still another alternative manufacturing scheme, the solution of silicone adhesive and drug is cast directly into the acrylic pressure sensitive adhesive/release liner subassembly and dried. A backing is then applied to form the completed laminated composite.

It has surprisingly been found that, in the treatment of nicotine dependence, women respond more favorably to a patch that combines nicotine and mecaylamine than to a patch that contains either nicotine or mecamylamine alone. The patch can be administered while the woman continues to smoke and then ceases smoking or if she chooses to stop smoking at the same time as beginning treatment.

For treatment of nicotine dependence, the patches of the invention are typically worn for a total period of about 3 to 16 weeks. During the first 1 to 4 weeks, preferably 2 to 3 weeks, the patent is allowed to smoke as desired. During the remainder of the treatment, i.e. two to 12 weeks, preferably 4 to 8 weeks, the patient is advised to not smoke.

EXAMPLES

The following examples further illustrate the patches of the invention and the process used to make them. These examples are not intended to limit the invention in any manner.

Example 1

Preparation and Testing of Nicotine Patch

Nicotine was added to a hexane solution of Dow Corning BIO-PSA amine-compatible silicone pressure sensitive adhesive to a level of approximately 12% by weight based on the combined dry weight of adhesive and nicotine. The resulting hexane solution of adhesive and nicotine was coated onto a 3M Scotchpak 1109 polyester/polyolefin backing at 13.8 mg/cm$^2$ (1.63 mg/cm$^2$ nicotine and 12.17 mg/cm$^2$ adhesive) and the coated backing was dried at 30° C. to 40° C. for about 3 min.

National Starch DuroTak 87 2194 acrylic solution pressure sensitive adhesive was coated onto a 125 micron thick Daubert Coater Products 1-5 PESTR (Matte)-164Z siliconized polyester release liner at 13.18 mg/cm$^2$ and the coated release liner was dried at 100° C. for about 10 min.

The dried silicone adhesive/nicotine-coated backing layer subassembly was then laminated to the dried acrylic adhesive-coated release liner subassembly to form a four-layer laminated composite. Following lamination, the nicotine distributes itself (via diffusion) uniformly within the adjacent silicone adhesive layer and acrylic adhesive layer of the composite. The concentration of nicotine within the layers was about 6% (w/w) after equilibration.

In vitro nicotine flux from the laminated composite was determined at 320 C through human cadaver epidermis into an infinite sink using modified Franz glass diffusion cells. Nicotine assays were made by HPLC.

Figure 2:
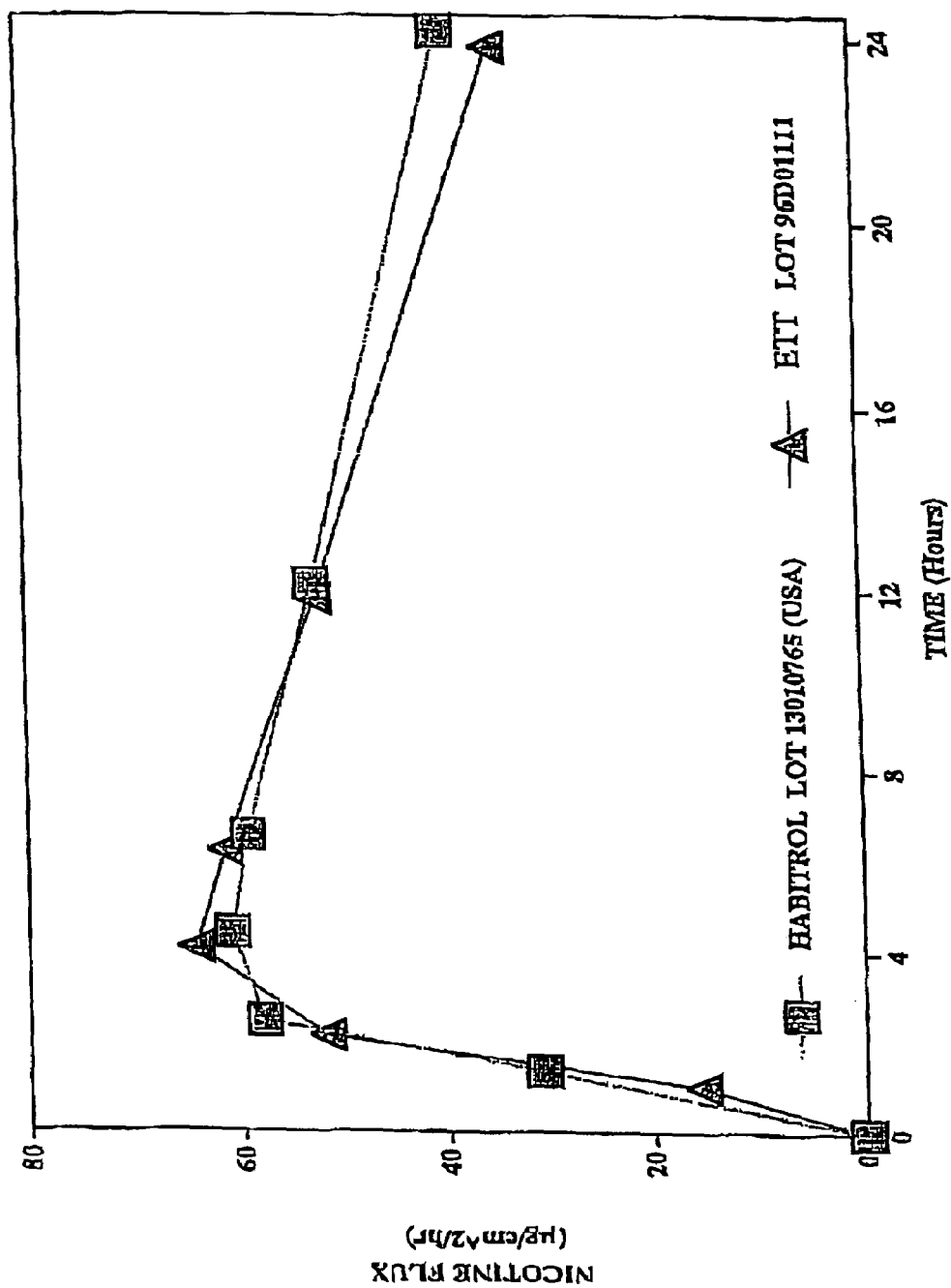
FIGS. 2–6 are graphs of the results of the in vitro skin flux tests described in the examples.

For comparison purposes the flux of nicotine from commercial Habitrol3 21 mg/day patches was determined using the same test procedure. FIG. 2 is a graph of the nicotine flux from the composite of the example and from the Habitrol3 patches versus time.

Example 2

Preparation and Testing of Nicotine/Mecamylamine Patches

Nicotine and mecamylamine were added to a hexane solution of Dow Corning BIO-PSA amine compatible silicone pressure sensitive adhesive. Two batches were made: one contained approximately 10% nicotine and 6.4% mecamylamine based on the total dry weight of the adhesive and the two drugs; and a second contained approximately 10% nicotine and 4.2% mecamylamine, based on the total dry weight of the adhesive and the two drugs. The batches were separately coated onto a 3M Scotchpak 1109 polyester/polyoefin backing film at 9.6 mg/cm$^2$ (0.96 mg/cm$^2$ nicotine, 0.61 mg/cm$^2$ mecamylamine, 8.03 mg/cm$^2$ adhesive for the first batch; 0.96 mg/cm$^2$ nicotine, 0.40 mg/cm$^2$ mecamylamine, 8.24 mg/cm$^2$ adhesive for the second batch) and then dried at 30–40° C. for about 2 min.

A blend of two National Starch DuroTak acrylic solution polymers, 87-2196 and 87-2516, 25% and 75% w/w, respectively, was made. The blend was coated at 8.0 mg/cm$^2$ onto a 75 micron thick Daubert Coater Products siliconized polyester release liner (1-3 PESTR (Matte)-164Z) and dried at about 100° C. for about 10 min.

The drug-containing silicone adhesive/backing subassembly was then laminated to the acrylic adhesive/release liner subassembly to form a four layer/laminated composite. After lamination the nicotine and mecamylamine distributed themselves uniformly within the adjacent adhesive layers. The concentration of the drugs in the adhesive layers after equilibration was: nicotine, 5.450% (w/w) and mecamylamine 3.47% (w/w) for the composite made from the first batch and 5.45% (w/w) and 2.27% (w/w), respectively, for the composite made from the second batch. Patches about 23 cm$^2$ in area were cut from the composites. These patches were designed to deliver 21 mg of nicotine and 6 mg of mecamylamine in 24 hr and 21 mg of nicotine and 3 mg of mecamylamine in 24 hr, respectively.

Figure 3:
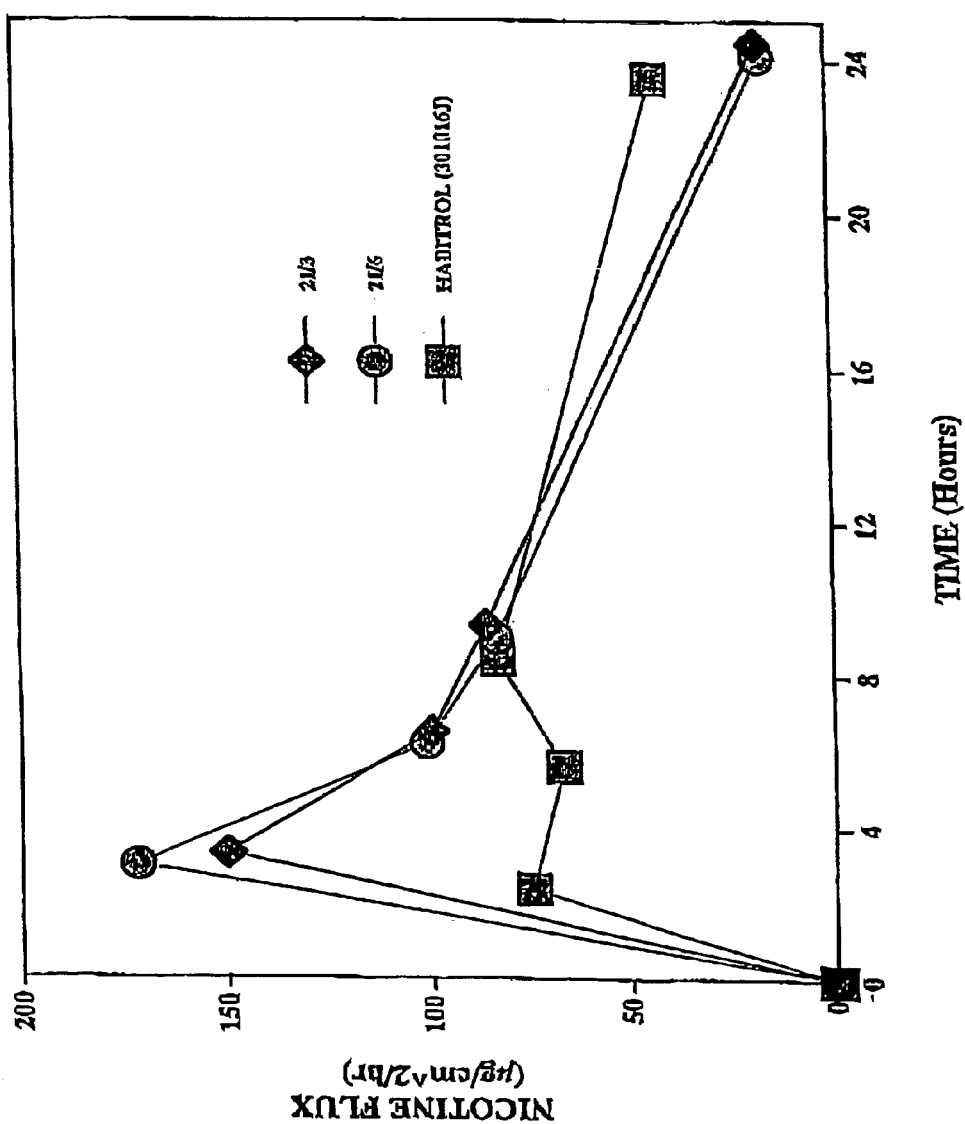
Figure 4:
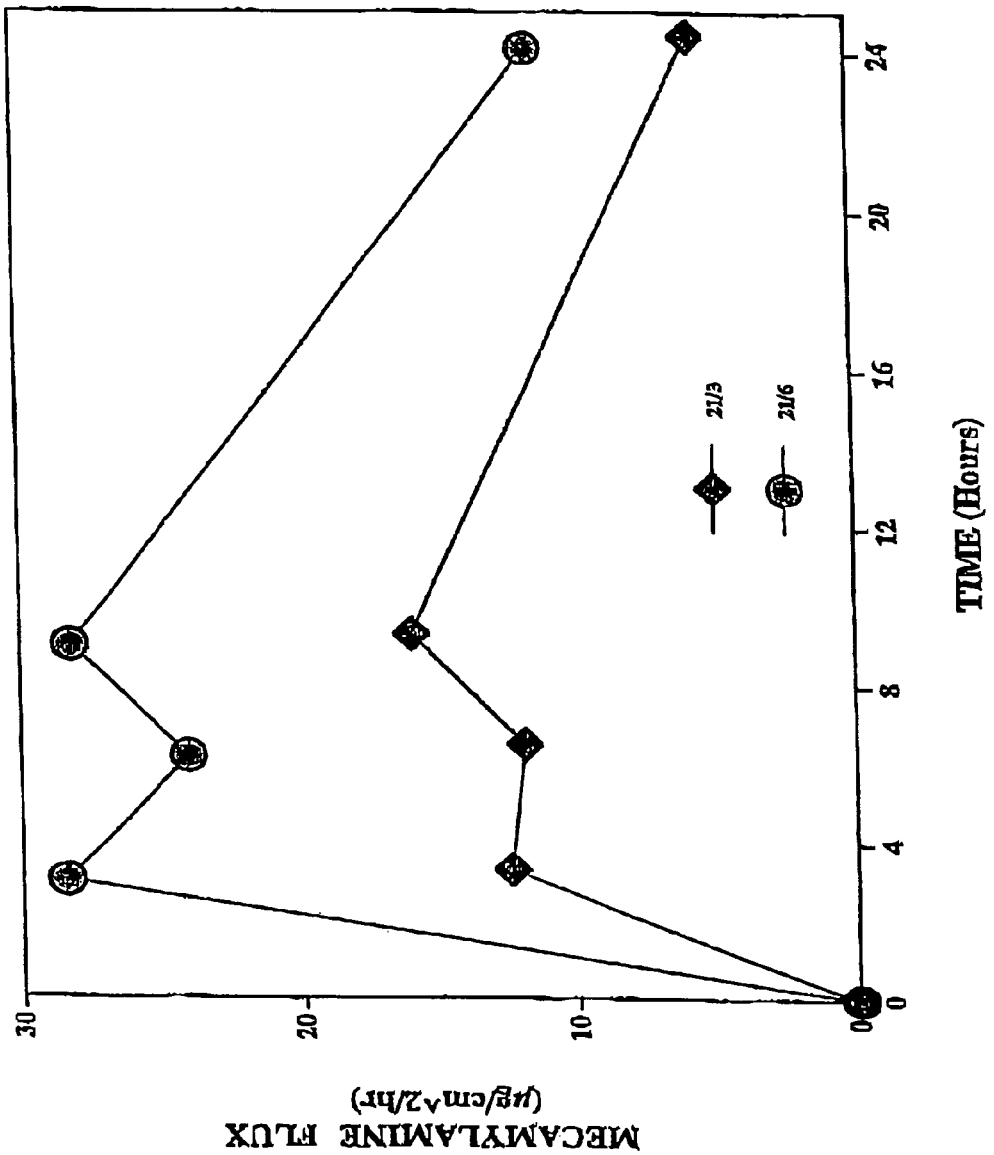

Nicotine and mecamylamine fluxes from the patches were determined using the procedure described Example 1. Mecamylamine assays were made by GC. FIG. 3 is a graph showing the nicotine flux from the patches versus time. Patches made from the first batch composite are designated 21/6; those from the second batch composite are designated 21/3. FIG. 4 similarly is a graph showing the mecamylamine flux from the patches.

Example 3

Preparation and Testing of Selegiline Patch

Selegiline was added to a hexane solution of Dow Corning BIO-PSA® amine-compatible silicone pressure sensitive adhesive to a concentration of approximately 10% by weight based on the combined dry weight of adhesive and selegiline. The resulting hexane solution of adhesive and selegiline was coated on 3M Scotchpak 1109 polyester/polyolefin backing at 10.0 mg/cm$^2$ (1.0 mg/cm$^2$ selegiline and 9.0 mg/cm² adhesive) and the coated backing was dried at 300 C to 400 C for about 3 minutes.

National Starch DuroTak® 87-2194 acrylic solution pressure sensitive adhesive was coated onto a 125 micron thick Daubert Coated Products 1-5 PESTER (Matte)-164Z siliconized polyester release liner at 8.0 mg/cm² and the coated release liner was dried at about 1000 C for about 10 minutes.

The dried silicone adhesive/selegiline-coated backing layer subassembly was then laminated to the dried acrylic adhesive-coated release liner subassembly to form a four-layer laminated composite. Following lamination, the selegiline distributes itself (via diffusion) uniformly within the adjacent silicone adhesive layer and acrylic adhesive layer of the composite. The concentration of selegiline within the layers in about 5.5% (w/w) after equilibration.

Selegiline flux from the patches was determined using the procedure described in Example 1. Selegiline assays were made by HPLC.

Figure 5:
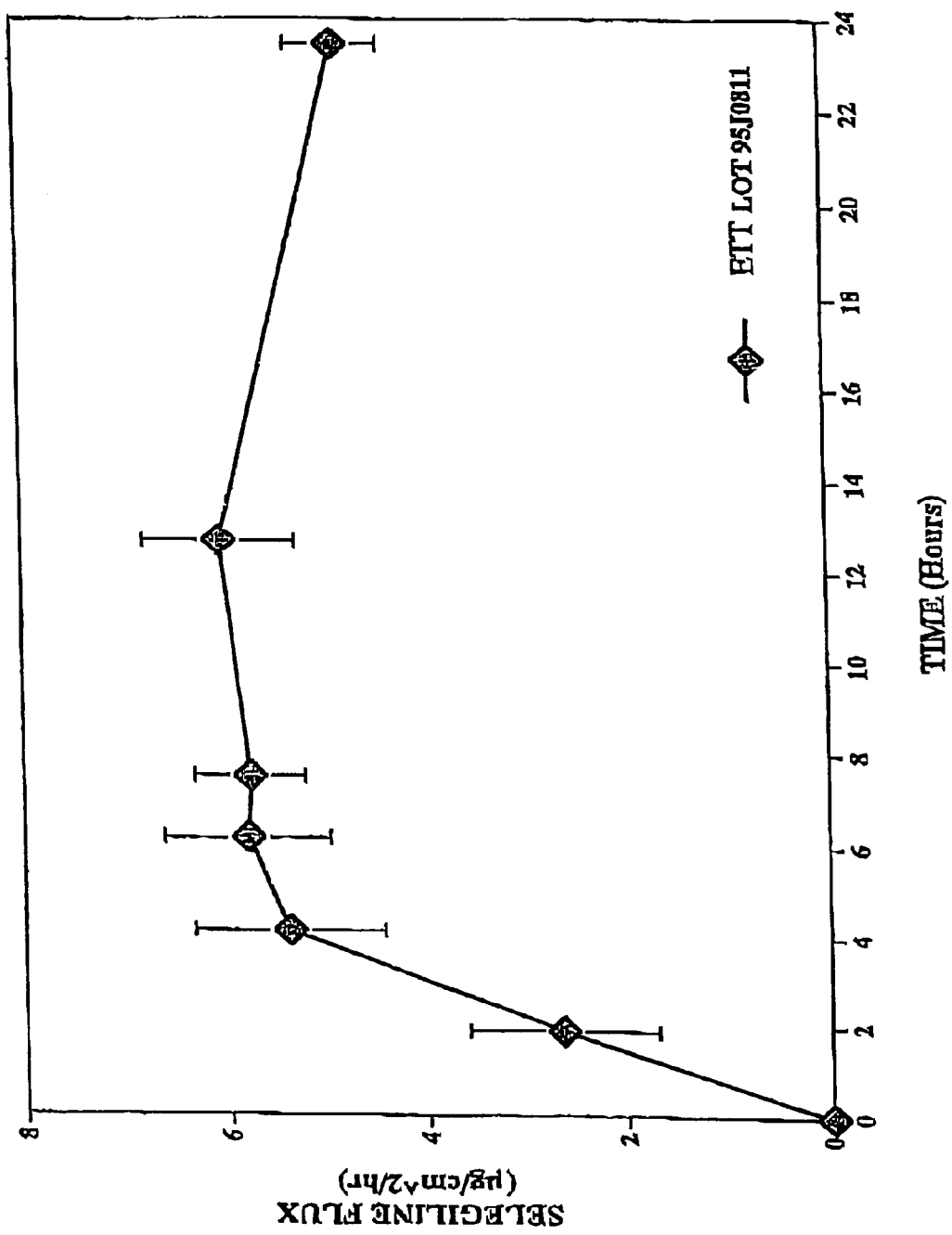

FIG. 5 is a graph of the selegiline flux from the composite of this example versus time.

Example 4

Preparation and Testing of Mecamylamine Patch

Mecamylamine was added to a hexane solution of Dow Corning BIO-PSA® amine-compatible silicone pressure sensitive adhesive to a concentration of approximately 6.3% by weight based on the combined dry weight of adhesive and mecamylamine. The resulting hexane solution of adhesive and mecamylamine was coated on 3M Scotchpack 1109 polyester/polyolefin backing at 9.6 mg/cm² (0.61 mg/cm² mecamylamine and 8.99 mg/cm² adhesive) and the coating backed was dried at 300 C to 400 C for about 3 minutes.

A blend of two National Starch DuroTak® acrylic solution polymers, 87-2196 and 87-2516, 25% and 75% w/w, respectively, was made. The blend was coated onto a 75 micron thick Daubert Coated Products 1-2 PESTR (Matte)-164Z siliconized polyester release liner at 8.0 mg/cm² and the coated release liner was dried at about 1000 C for about 10 minutes.

The dried silicone adhesive/mecamylamine-coated backing layer subassembly was then laminated to the dried acrylic adhesive-coated release liner subassembly to form a four-layer laminated composite. Following lamination, the mecamylamine distributes itself (via diffusion) uniformly within the adjacent silicone adhesive layer and acrylic adhesive layer of the composite. The concentration of mecamylamine within the layers is about 3.47% (w/w) after equilibration. Patches about 23 cm² in area were cut from the composites. These patches were designed to deliver 6 mg of mecamylamine in 24 hr.

Figure 6:
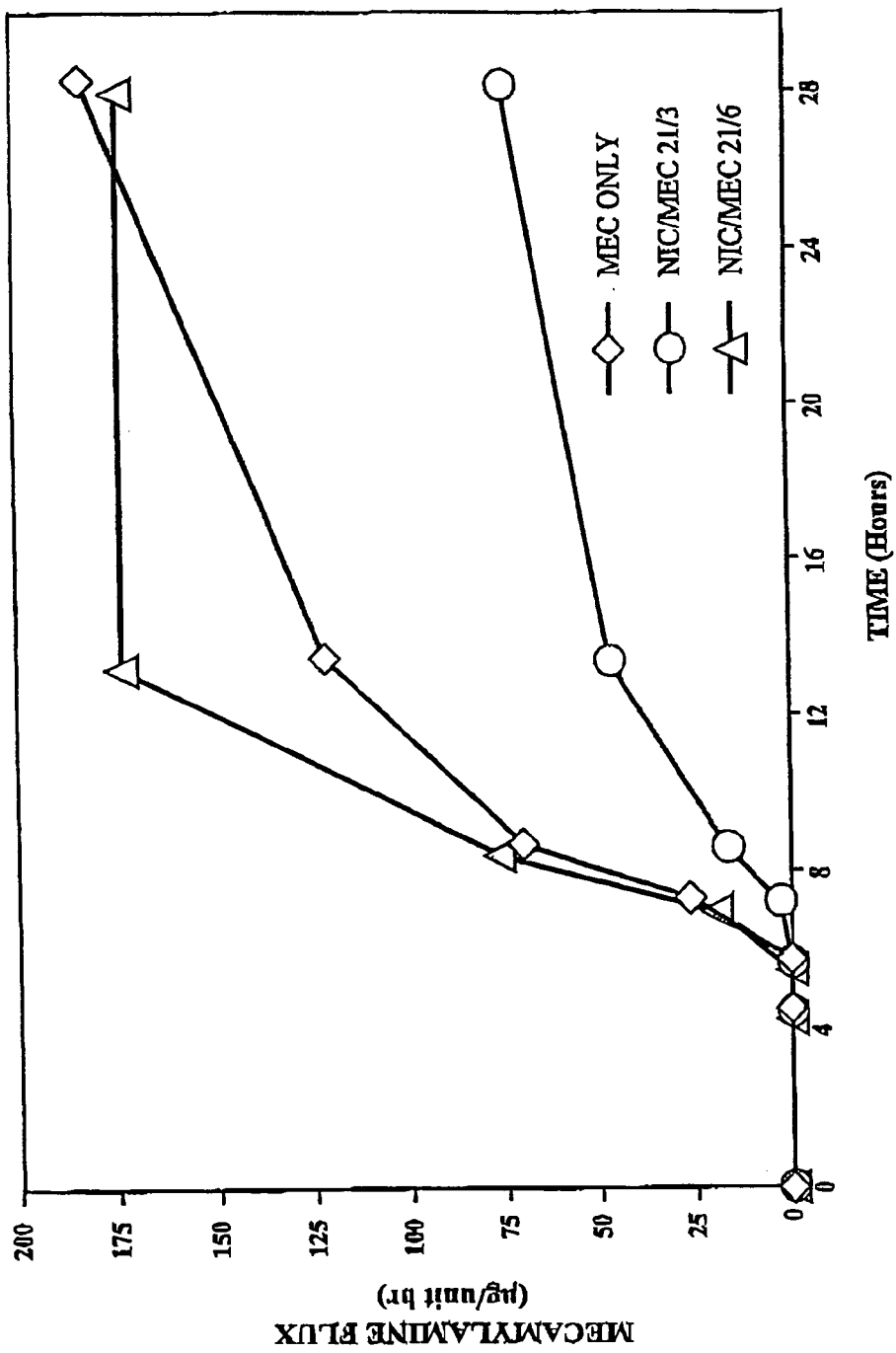

Mecamylamine flux from the patches was determined using the procedure described in Example 1. The mecamylamine assay was done by gas chromatography. FIG. 6 is a graph of the mecamylamine flux from the composite of this example versus time; mecamylamine flux through the same section of cadaver skin from the 21/3 and 21/6 compositions of Example 2 are shown for comparison.

Study A.

Patches made according to Examples 1, 2 and 4 and a placebo patch were subject to a clinical study. The study was a multi-center double-blind, randomized parallel group study. Patients were randomized to receive one of five treatments: nicotine/mecamylamine 21/6; nicotine/mecamylamine 21/3); nicotine (21 mg/24 hr); mecamylamine (6 mg/24 hr) and placebo. Patches were applied daily for the first six weeks of the study. Patients were instructed to continue smoking for the first two weeks and to stop smoking thereafter.

Among the efficacy parameters monitored during the study were tour week continuous abstinence after the quit smoking date, nicotine plasma concentration and ad hoc smoking during the treatment period.

Table 1 below provides the overall abstinence data for the study. In the table "N" represents the number of patients, "No" indicates non-abstinence and "Yes" indicates abstinence. As indicated the nicotine/mecamylamine 21/6 gave the highest abstinence.

TABLE 1

|  | Overall | 21/6 | 21/3 | 21/0 | 0/6 | Pla |
|---|---|---|---|---|---|---|
| N: | 705 | 142 | 141 | 141 | 140 | 141 |
| No | 82% | 74% | 79% | 79% | 82% | 92% |
| Yes | 18% | 26% | 21% | 21% | 18% | 8% |

Figure 7:
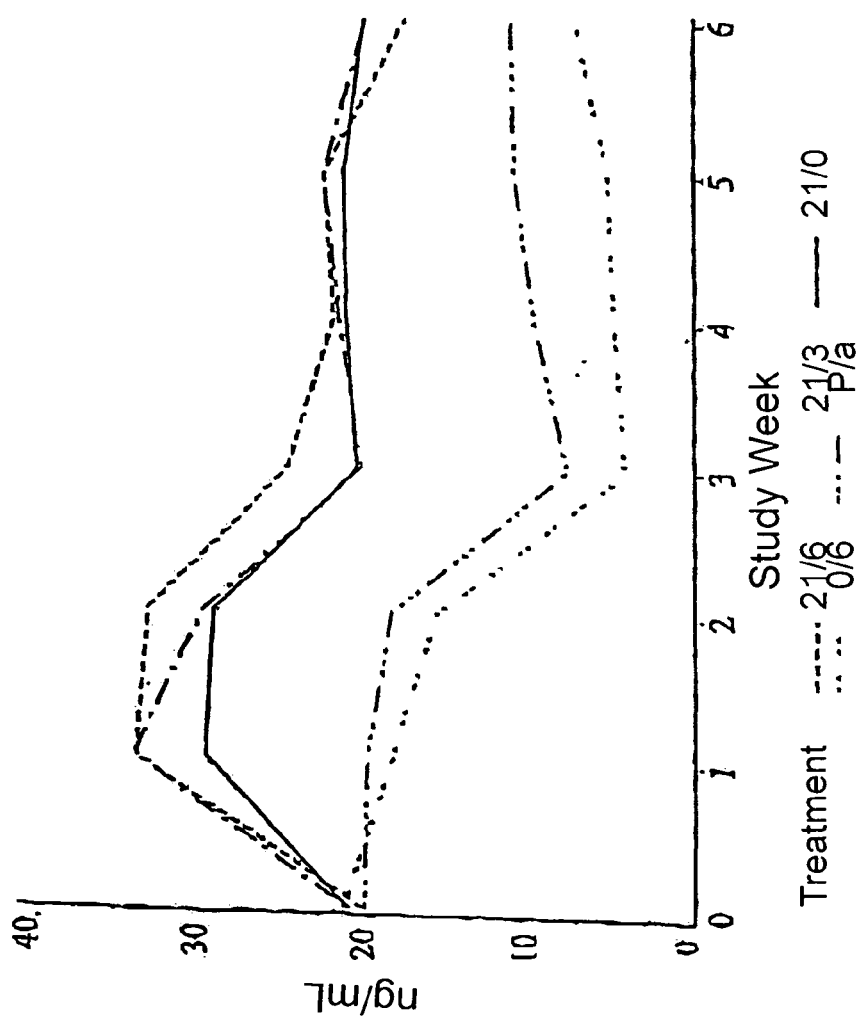
FIGS. 7 and 8 are graphs of the results of the clinical studies described in the examples.
Figure 8:
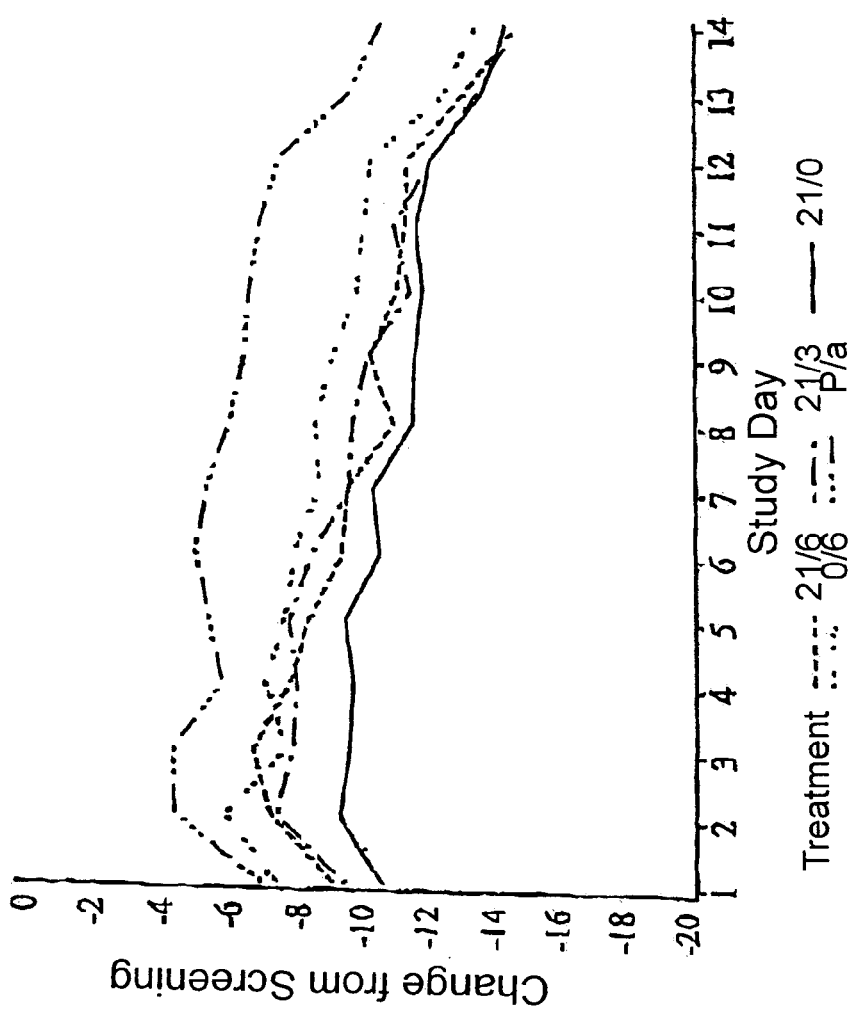

FIG. 7 is a graph showing the mean nicotine plasma concentrations in ng/ml of the patients by treatment and time. As shown, the mecamylamine only patch (0/6) produced a steady decline in nicotine levels even during the initial two-week period of the study. FIG. 8 is a graph showing the mean observed change in the number of cigarettes smoked by treatment and day. Surprisingly, the number of cigarettes smoked did not increase with the mecamylamine only (0/6) treatment, as the literature reports that oral mecamylamine administration increased ad hoc cigarette consumption.

Study B.

A second multi-center, double-blind, randomized parallel group clinical study was conducted. Patients were randomized to receive one of three treatments: nicotine/mecaylamine 21/6; nicotine/mecamylamine 21/3, and nicotine (21 mg/24 hr). Patient instructions were the same as in the first study.

The abstinence data for this study are summarized in Table 2. In this study the nicotine/mecamylamine combination was again more effective than nicotine alone.

TABLE 2

| Treatment: | 21/6 | 21/3 | 21/0 |
|---|---|---|---|
| N | 180 | 180 | 180 |
| Abstinence | 29% | 29% | 23% |

A detailed examination of the data the clinical studies yielded a surprising difference in abstinence rates for females and males. In both studies, the abstinence rate for females in the 21/6 treatment group was 31% compared to the 21/0 treatment group rates of 17% in the first study and 18% in the second study. These gender specific data are summarized in Table 3.

TABLE 3

| Study | Gender |  | 21/6 | 21/3 | 21/0 | 0/6 | Plac |
|---|---|---|---|---|---|---|---|
| First | Female | N | 70 | 67 | 63 | 75 | 74 |
|  |  | % Abst. | 31 | 16 | 17 | 17 | 9 |
|  | Male | N | 72 | 74 | 78 | 65 | 67 |
|  |  | % Abst. | 21 | 26 | 24 | 18 | 6 |

TABLE 3-continued

| Study | Gender | | 21/6 | 21/3 | 21/0 | 0/6 | Plac |
|---|---|---|---|---|---|---|---|
| Second | Female | N | 93 | 96 | 91 | | |
| | | % Abst. | 31 | 29 | 18 | | |
| | Male | N | 87 | 84 | 89 | | |
| | | % Abst. | 28 | 29 | 28 | | |

N = number of subjects in study.
% Abst. = Four-week continuous abstinence results.

Modifications of the above described modes for carrying out the invention that are obvious to persons of skill in the transdermal patch art are intended to be within the scope of the following claims. All publication, patent applications and patents noted above are hereby incorporated by reference.

What is claimed is:

1. A transdermal patch for administering a volatile liquid drug transdermally to a patient comprising
    a) a top backing layer that is impermeable to the drug;
    b) an intermediate, cast, amine-compatible solid silicone adhesive layer which underlies the backing layer, has a thickness of from about 25 microns to about 100 microns, and contains from about 5 to about 50 wt. % of the drug based on the total dry weight of the drug and adhesive, and is a source in the patch of the drug;
    c) a solid acrylic adhesive layer having a thickness of from about 25 microns to about 100 microns and comprising a copolymer of (i) vinyl acetate, (ii) acrylic acid, and (iii) at least one monomer selected from the group consisting of acrylate and methacrylate, and which underlies and is in diffusional contact with the silicone adhesive layer; and
    d) a removable release liner layer underlying the acrylic adhesive layer, wherein the relative thickness of layers "b" and "c", and the concentration of drug initially present in layer "b" is selected to provide a drug flux profile which is characterized by an initial period during which the flux rises to a level suitable for administering a therapeutic amount of the drug, and a second period during which the drug flux is sustained above said level, said second period lasting for at least twice as long as said initial period, and wherein the amount of drug in the patch is sufficient to provide a therapeutically effective amount of drug to the patient over a period of at least about several hours and wherein the drug is a combination of nicotine and mecamylamine and the patch is capable of administering 0.2 to 1.5 mg nicotine per hour and 0.02 to 1 mg mecamylamine per hour to the patient.

2. The patch of claim 1, wherein the silicone adhesive layer comprises a silicone pressure sensitive adhesive.

3. The patch of claim 1, wherein the patch contains an amount of drug sufficient to provide administration of the drug for a period of up to about 72 hours.

* * * * *